(12) United States Patent
Du et al.

(10) Patent No.: US 7,532,703 B2
(45) Date of Patent: May 12, 2009

(54) ENERGY DISCRIMINATING DETECTOR WITH DIRECT CONVERSION LAYER AND INDIRECT CONVERSION LAYER

(75) Inventors: Yanfeng Du, Rexford, NY (US); J. Eric Tkaczyk, Delanson, NY (US); David M. Hoffman, New Berlin, WI (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/692,304

(22) Filed: Mar. 28, 2007

(65) Prior Publication Data

US 2008/0240339 A1 Oct. 2, 2008

(51) Int. Cl.
*A61B 6/00* (2006.01)
(52) U.S. Cl. .................. 378/19; 378/98.8; 378/116
(58) Field of Classification Search ............... 378/4–27, 378/62, 98.8, 98.9, 98.11, 98.12, 116; 250/370.08, 250/370.09, 370.11
See application file for complete search history.

(56) References Cited

U.S. PATENT DOCUMENTS

| 7,105,828 | B2 * | 9/2006 | Unger et al. | 250/370.09 |
| 7,129,498 | B2 * | 10/2006 | Hoffman | 250/370.09 |
| 2006/0045236 | A1 * | 3/2006 | Hoffman | 378/19 |
| 2008/0230709 | A1 * | 9/2008 | Tkaczyk et al. | 250/370.09 |

* cited by examiner

*Primary Examiner*—Courtney Thomas
(74) *Attorney, Agent, or Firm*—Joseph J. Christian (57) ABSTRACT

A diagnostic imaging system includes a high frequency electromagnetic energy source that emits a beam of high frequency electromagnetic energy toward an object to be imaged. An energy discriminating (ED) detector receives high frequency electromagnetic energy emitted by the high frequency electromagnetic energy source. The ED detector includes a direct conversion layer dynamically operable in a photon counting mode in one view and in an integrating mode in another view and an indirect conversion layer. A data acquisition system (DAS) is operably connected to the ED detector and a computer operably connected to the DAS.

21 Claims, 7 Drawing Sheets

ENERGY DISCRIMINATING DETECTOR WITH DIRECT CONVERSION LAYER AND INDIRECT CONVERSION LAYER

BACKGROUND OF THE INVENTION

The present invention relates generally to diagnostic imaging and, more particularly, to a method and apparatus of high flux rate imaging with energy discrimination, such as in computed tomography (CT) applications.

Exemplary diagnostics devices comprise x-ray systems, magnetic resonance (MR) systems, ultrasound systems, computed tomography (CT) systems, positron emission tomography (PET) systems, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. The characteristic of this system using scintillators and photodiodes is that the output signal passed to the system is proportional to the x-ray energy incident to the detector during an integration view time. Some exemplary systems provide instead a photon counting detection mechanism whereby the signal passed to the system is proportional to the number of x-ray photons. Since the spectrum of the incident x-ray flux has a breadth in energy there may be a considerable difference in the number of x-ray photons and the total energy of the photons. The photon counting detector has improved dose efficiency. In addition, the photon counting detector can be configured with additional energy thresholds to distinguish photons at different energy thresholds and count these in separate registers. Generally, photon counting systems used for CT imaging use direct conversion sensor materials because the signal charge created per x-ray may be much greater than that of a scintillator/photodiode sensor.

An exemplary CT imaging system comprises an energy discriminating (ED) and/or multi energy (ME) CT imaging system that may be referred to as an EDCT and/or MECT imaging system. The EDCT and/or MECT imaging system in an example is configured to be responsive to different x-ray spectra. For example, a conventional third generation CT system acquires projections sequentially at different x-ray tube potentials. Two scans in an example are acquired either back to back or interleaved in which the tube operates at 80 kVp and 160 kVp potentials. Special filters in an example are placed between the x-ray source and the detector such that different detector rows collect projections of different x-ray energy spectra. The special filters that shape the x-ray spectrum in an example can be used for two scans that are acquired either back to back or interleaved. Energy sensitive detectors in an example are used such that each x-ray photon reaching the detector is recorded with its photon energy.

Exemplary ways to obtain the measurements comprise: (1) scan with two distinctive energy spectra, (2) detect photon energy according to the depth from the incident surface for energy deposition in the detector, and (3) photon counting with multiple energy thresholds. EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and (2) the photoelectric effect. The detected signals from two energy regions provide sufficient information to resolve the energy dependence of the material being imaged. Furthermore, detected signals from the two energy regions provide sufficient information to determine the relative composition of an object composed of two materials.

The conventional basis material decomposition (BMD) algorithm is based on the concept that in the energy region for medical CT, the x-ray attenuation of any given material can be represented by a proper density mix of two other materials, referred to as the basis materials. Based on the projections acquired at the two incident x-ray spectra, the BMD algorithm computes two sets of new projections, corresponding to two new CT images that each represents the equivalent density of one of the basis materials. Since a material density is independent of x-ray photon energy, these images are approximately free of beam-hardening artifacts. An operator can choose the basis material to target a certain material of interest, for example, to enhance the image contrast.

An energy discriminating (ED) detector may comprise a plurality of integrating layers. For dose efficiency, it may be desirable to have the total x-ray spectra incident to the detector absorbed in the combination of the layers. Conventionally, two layers are used where the low energy portion of the spectra is absorbed in a thin top layer and high energy portion of the spectra is absorbed in a thick bottom layer. The top and bottom layers may comprise direct conversion layers, for example, with a relative thickness in a layer that may lead to polarization effects, instability, and/or non-linear responses at relatively high x-ray flux. Thick layers of direct conversion material may require a longer transport distance for charge carriers and therefore a greater amount of charge trapping. An ED detector may comprise a plurality of scintillator and photodiode layers, for example, with interaction between the top and bottom layers that may add noise for the low and high energy signals.

Alternatively, an ED detector may comprise a single photon counting layer with two or more energy bins. At low incident flux, a single-layer, photon counting detector may generally perform material basis decomposition at a lower dose than an implementation of the ED detector of multiple integrating layers. Such a photon-counting layer needs to have sufficient thickness to absorb a substantial fraction of the incident x-ray flux. At typical relatively high thicknesses, this photon-counting layer may exhibit polarization effects, instability, and/or non-linear response at relatively high x-ray flux.

These undesirable effects are caused in the thick layer due to the fact that electrical charge carriers become trapped in the layer due to the long transport distance between the x-ray absorption point and the contacts. Furthermore, a relatively thick, single-layer photon-counting detector saturates due to pile-up when x-ray photons arrive at the detector at a greater pace than the readout electronics of the detector can register the x-ray photons.

Therefore, it would be desirable to design an apparatus and method to promote a reduction in one or more of energy discriminating (ED) detector layer thickness, ED detector polarization, instability, non-linearity, and/or noise. It would be further desirable to have the improved dose efficiency of a photon-counting system and an ability to mitigate the saturation phenomena of pile-up.

BRIEF DESCRIPTION OF THE INVENTION

The invention in an implementation encompasses a CT system that overcomes the aforementioned drawbacks. A CT detector includes a direct conversion layer and an indirect conversion layer. The direct conversion layer is dynamically operable in either a photon counting mode or an integration mode.

Therefore, according to an aspect of the present invention, a diagnostic imaging system includes a high frequency electromagnetic energy source that emits a beam of high frequency electromagnetic energy toward an object to be imaged. An energy discriminating (ED) detector receives high frequency electromagnetic energy emitted by the high frequency electromagnetic energy source. The ED detector includes a direct conversion layer dynamically operable in a photon counting mode in one view and in an integrating mode in another view and an indirect conversion layer. A data acquisition system (DAS) is operably connected to the ED detector and a computer operably connected to the DAS.

According to another aspect of the present invention, a diagnostic imaging detector includes a stacked arrangement of a direct conversion layer and an indirect conversion layer. The direct conversion layer is located between a radiographic energy source and the indirect conversion layer and is operable dynamically from a photon counting mode in one view to an integrating mode in another view.

According to yet another aspect of the present invention, a method of CT imaging includes emitting an x-ray beam through a subject to be scanned and toward a CT detector having a direct conversion layer and an indirect conversion layer and acquiring energy data from the direct conversion layer and from the indirect conversion layer. The method further includes determining a photon count rate based on the acquired energy data and dynamically configuring the direct conversion layer to operate in one of a photon counting mode and an integrating mode based on the photon count rate.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Exemplary diagnostics devices comprise x-ray systems, magnetic resonance (MR) systems, ultrasound systems, computed tomography (CT) systems, positron emission tomography (PET) systems, and other types of imaging systems. Exemplary applications of x-ray sources comprise imaging, medical, security, and industrial inspection applications. The operating environment of an exemplary implementation comprises a 64-slice CT system. However, it will be appreciated by those skilled in the art that an exemplary implementation is applicable for use with single-slice or other multi-slice configurations. Moreover, an exemplary implementation is employable for the detection and conversion of x-rays. However, one skilled in the art will further appreciate that an exemplary implementation is employable for the detection and conversion of other high frequency electromagnetic energy and/or high frequency polychromatic electromagnetic energy. An exemplary implementation is employable with a "third generation" CT scanner and/or other CT systems.

Figure 1:
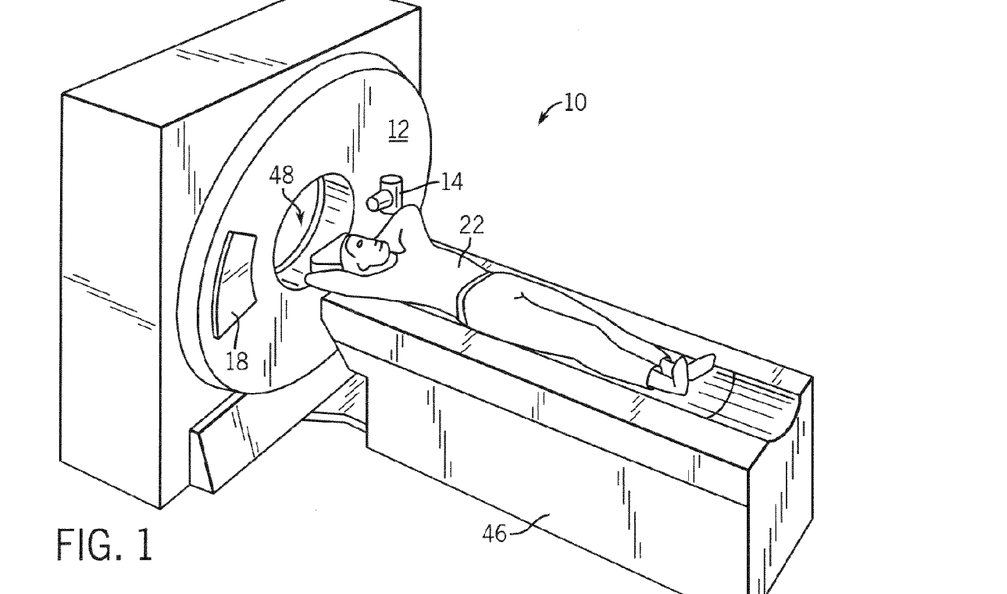
FIG. 1 is a pictorial view of an implementation of a CT imaging system.
Figure 2:
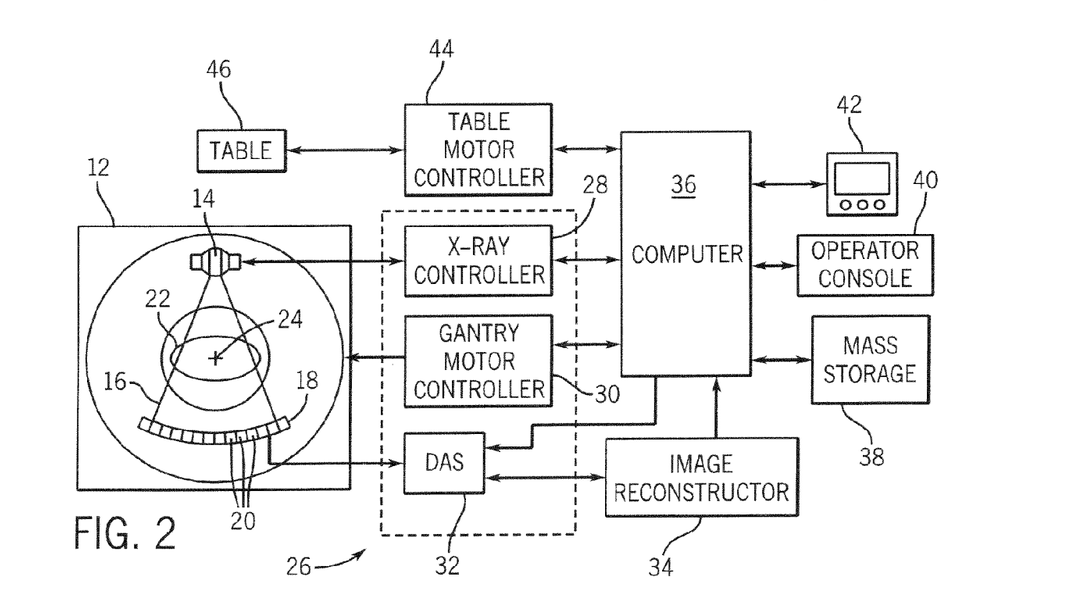
FIG. 2 is a block schematic diagram of an implementation of the system of FIG. 1.
Figure 3:
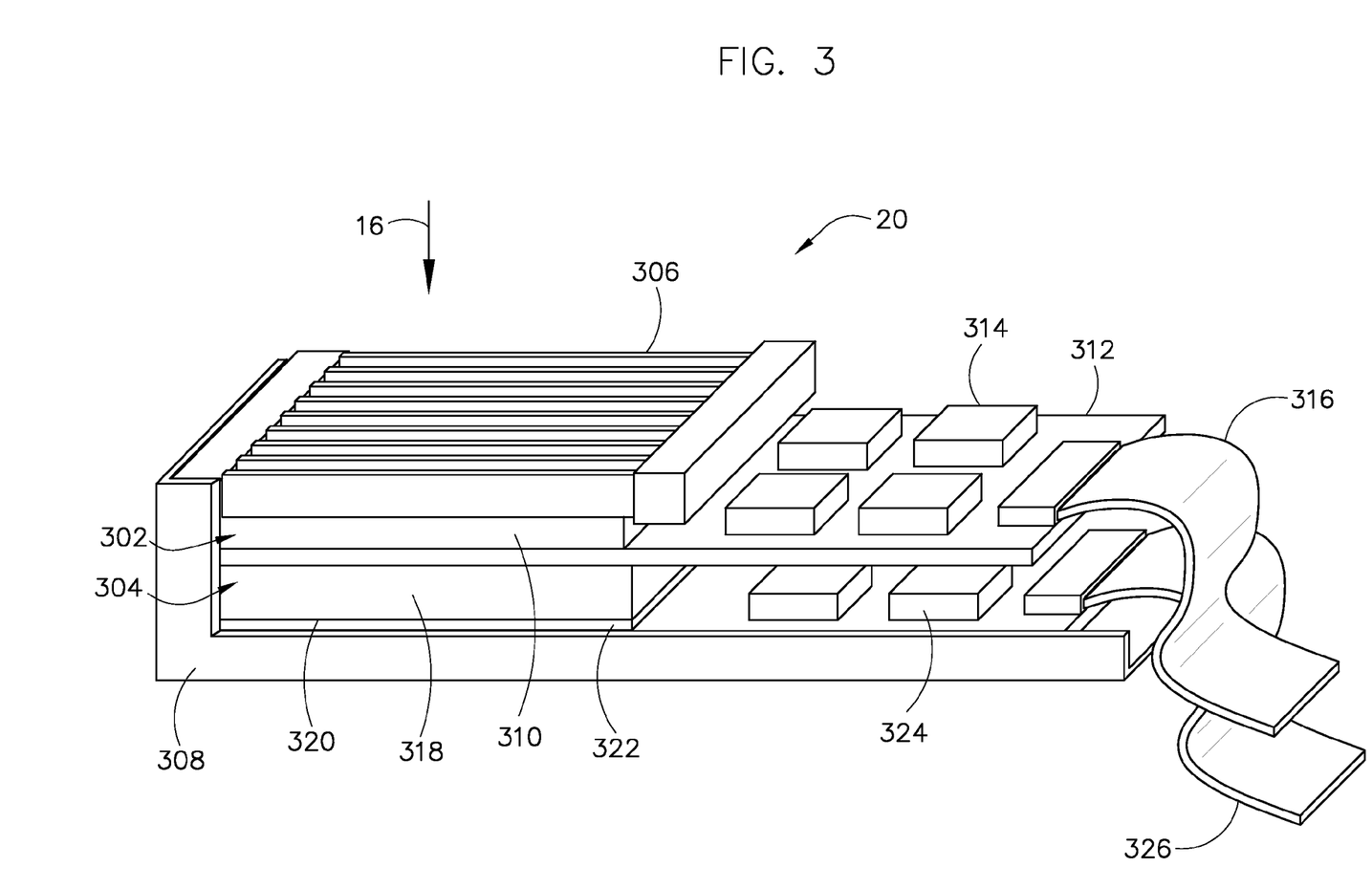
FIG. 3 is a representation of a top perspective view of an energy discriminating (ED) detector of an implementation of the system of FIG. 1.
Figure 4:
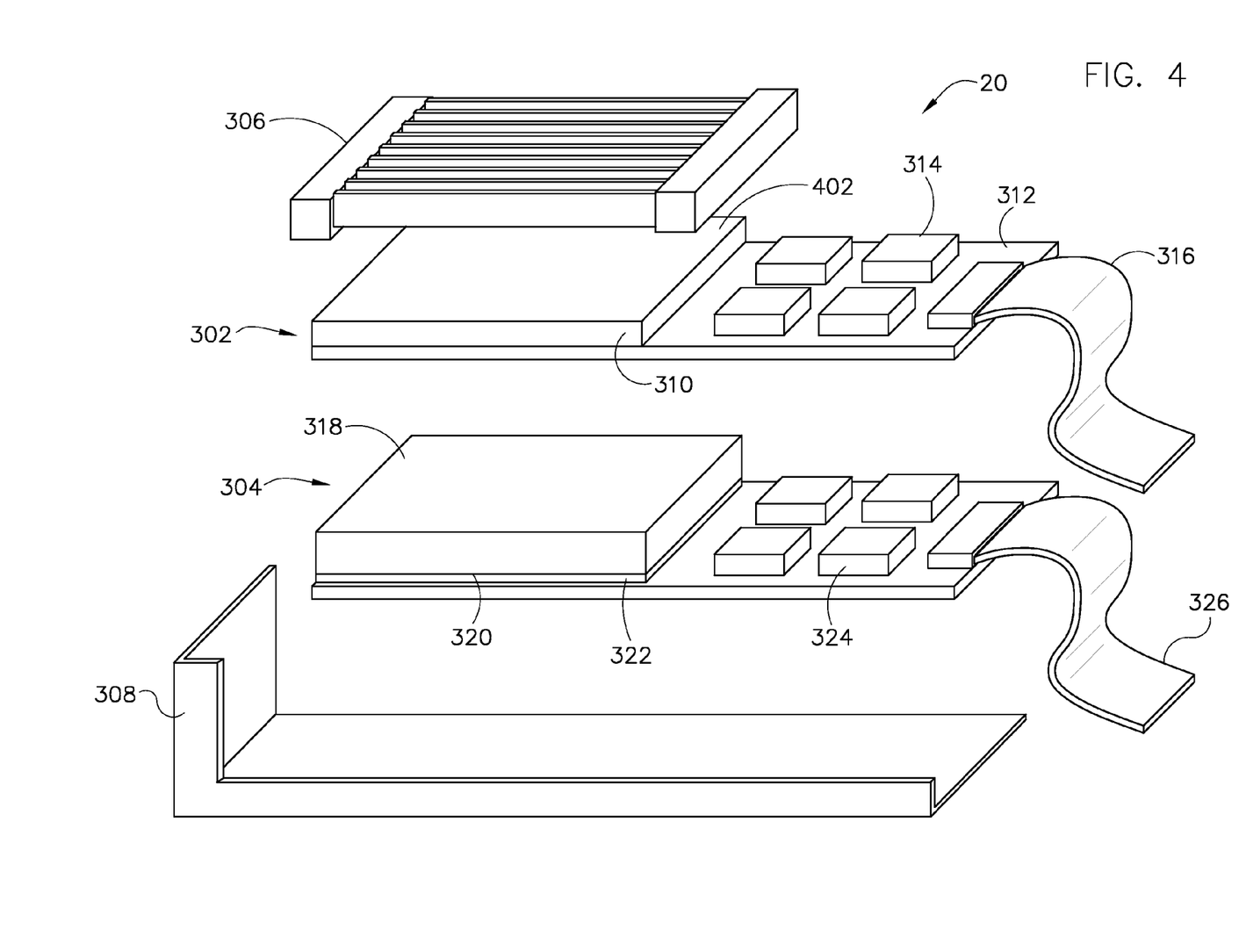
FIG. 4 is similar to FIG. 3 and further represents a partially exploded view of the ED detector.

Referring to FIGS. 1 and 2, a diagnostic and/or computed tomography (CT) imaging system 10 is shown as including a gantry 12 representative of a "third generation" CT scanner. The CT imaging system 10 in an example comprises an energy discriminating (ED) and/or multi energy (ME) CT imaging system that may be referred to as an EDCT and/or MECT imaging system. Gantry 12 has an x-ray source 14 that projects a beam of x-rays 16 toward a detector array 18 on the opposite side of the gantry 12. Detector array 18 is formed by a plurality of detectors such as energy discriminating (ED) detectors 20 which together sense the projected x-rays that pass through a medical patient 22. Each ED detector 20 produces an electrical signal that represents the intensity of an impinging x-ray beam and hence the attenuated beam as it passes through the patient 22. The ED detector 20 in an example obtains ED readout from the beam of x-rays 16. During a scan to acquire x-ray projection data, gantry 12 and the components mounted thereon rotate about a center of rotation 24, as will be appreciated by those skilled in the art.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from the ED detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

EDCT/MECT provides energy discrimination and material characterization. For example, in the absence of object scatter, the system derives the behavior at any other energy based on the signal from two regions of photon energy in the spectrum: the low-energy and the high-energy portions of the incident x-ray spectrum. In an exemplary energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object 22 composed of two materials.

Referring to FIGS. 3 through 6, an exemplary ED detector 20 receives the beam of x-rays 16 at an upstream layer 302 and a downstream layer 304. The ED detector 20 in an example comprises a plurality of layers such as the upstream layer 302 and the downstream layer 304, a collimator 306, one or more supports 308, and one or more rails 602. The rail 602 in an example comprises a part of the ED detector 20 at which the detector 20 mounts. The rail 602 in an example is mounted to the gantry 12.

The upstream and downstream layers 302, 304 in an example comprise direct and indirect conversion layers. In an example, the upstream layer 302 comprises a direct conversion layer configurable to operate in either a photon counting mode or an integration mode and the downstream layer 304 comprises an indirect conversion layer. An illustrative presentation of an exemplary implementation of a direct conversion layer as the upstream layer 302 and an indirect conversion layer as the downstream layer 304 is presented with reference to FIGS. 3 through 5, for explanatory purposes.

A percentage of x-rays 16 that are incident to the detector 20 are absorbed in the upstream layer 302 and the remaining percentage is absorbed in the downstream layer 304. The absorption of x-rays in layers 302 and 304 is described by Poisson statistics such that the information available in each layer is increased with increase in the number of absorbed x-rays. In one embodiment, an optimal design of the layer thickness depends on the strategy to recombine the data from the two layers 302 and 304 to form a composite image that maximizes the total information. In the absence of saturation effects in the layers, an optimum statistical combination occurs where equal numbers of x-ray photons are absorbed in each layer. Consequently, the design of the layer thickness will account for the expected saturation level above which the layer will no longer provide useable data. The upstream layer 302 in an example stops less than seventy percent of incident photons of the beam of x-rays 16 and transmits greater than thirty percent of the incident photons of the beam of x-rays 16 to the downstream layer 304. In this example, the information in the composite image is roughly derived equally from both layers. In another example, the upstream layer 302 stops greater than seventy percent of incident photons of the beam of x-rays 16 and transmits less than thirty percent of the incident photons of the beam of x-rays 16 to the downstream layer 304. For this example, the information in the composite image is largely from the upstream layer 302 at flux level below the saturation threshold of the upstream layer 302. At high flux levels above the saturation threshold of the upstream layer 302, the downstream layer 304, which receives less absorbed x-ray flux, provides the information for the composite image.

Figure 5:
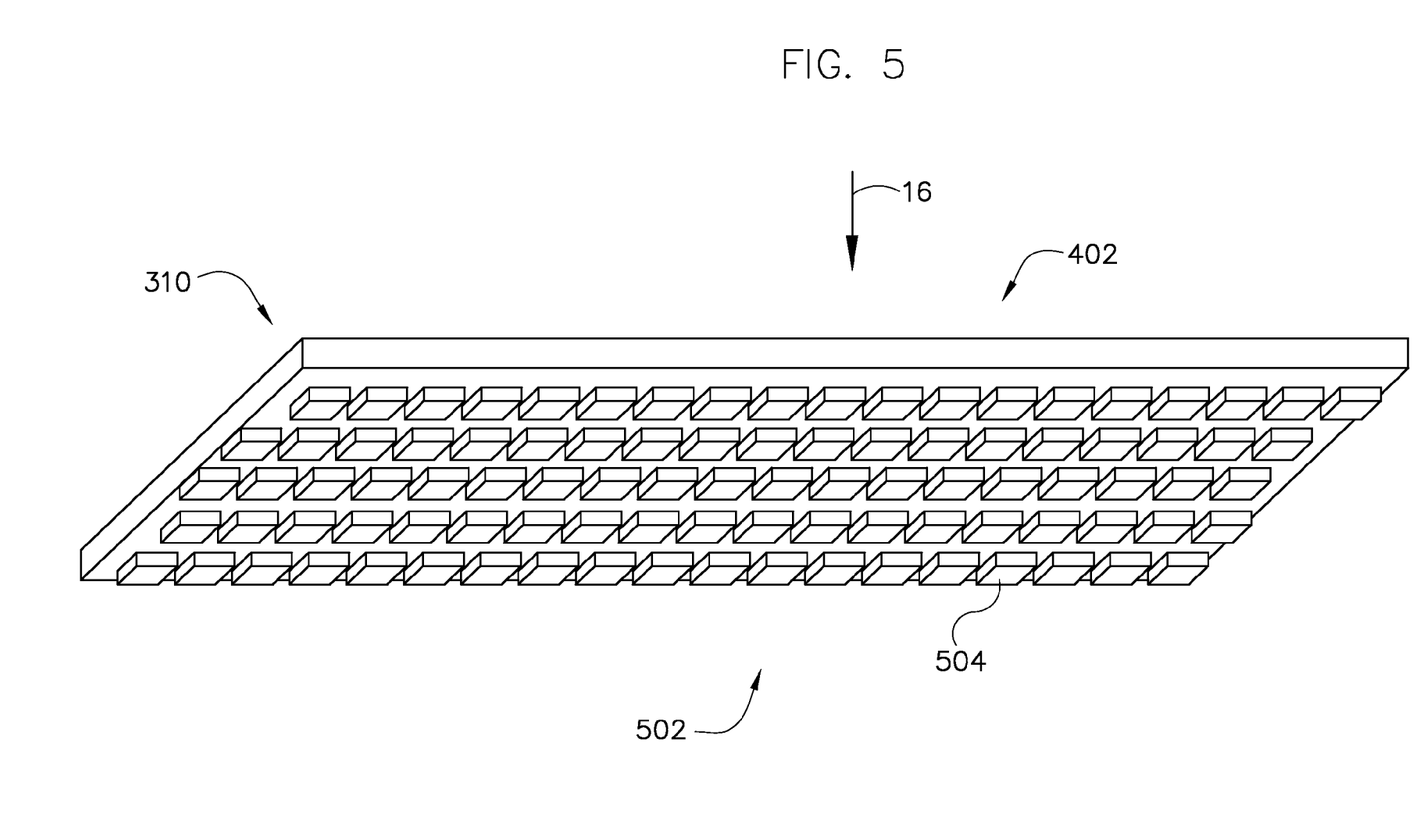
FIG. 5 is a representation of a bottom perspective view of a plurality of contacts on a downstream face of a direct conversion layer of the ED detector of FIG. 3.
Figure 6:
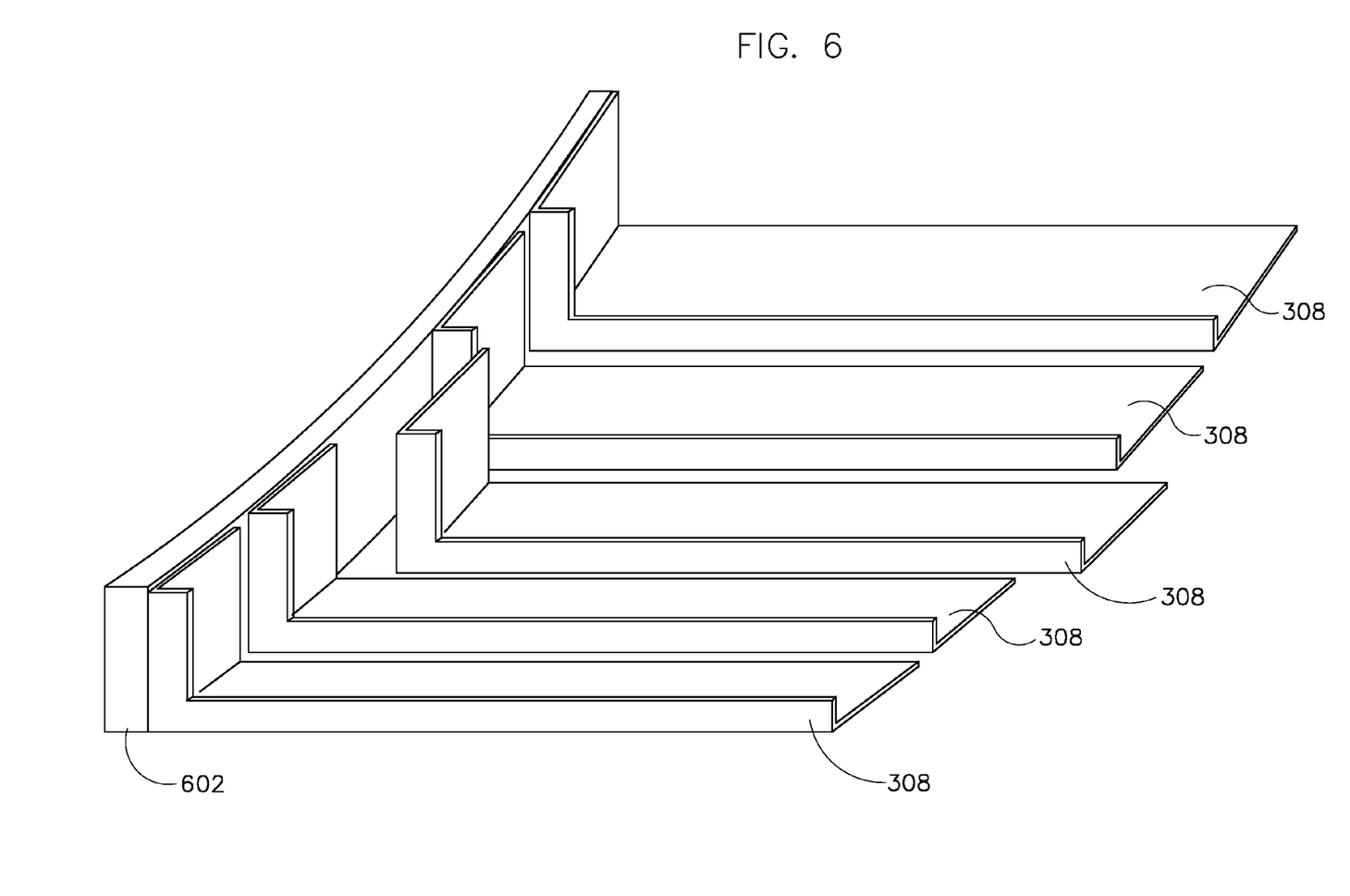
FIG. 6 is a representation of a top, partial, perspective, cutaway view of a rail and a plurality of removable supports of a respective plurality energy discriminating (ED) detectors of an implementation of the system of FIG. 1.

An exemplary direct conversion layer as the upstream layer 302 comprises a direct conversion layer, material, and/or sensor 310 and circuit board 312. The direct conversion sensor 310 in an example comprises a monolithic semiconductor crystal. For example, the direct conversion sensor 310 comprises cadmium telluride (CdTe) or cadmium zinc telluride (CZT) crystal with top and bottom side electrical contacts. The direct conversion sensor 310 in an example comprises a cathode 402 (FIG. 4) and an anode 502 (FIG. 5). The cathode 402 in an example comprises an upstream face and/or top side. An exemplary cathode 402 comprises a common cathode and/or unsegmented full cathode. The anode 502 in an example comprises a downstream face and/or bottom side. An exemplary anode 502 comprises a segmented anode and/or pixel array anode. The anode 502 in an example during an exemplary fabrication is formed to comprise a plurality of contacts, detection elements, electronically pixelated structures, and/or pixels 504.

An exemplary thickness of the direct conversion sensor 310 in a general direction of the beam of x-rays 16 is in an approximate range of 0.1 mm to 1.0 mm, for example, 0.2 mm. The material thickness of the direct conversion sensor 310 in an example serves and/or is sufficient to stop approximately one third to two thirds of the incident x-rays. In another example, the direct conversion sensor 310 as the upstream layer 302 comprises a thickness in the general direction of the beam of x-rays 16 is in an approximate range of 1.0 mm to 5.0 mm, for example, to stop ninety percent or more of the incident x-rays and transmit only a small and/or single digit percentage to the downstream layer 304, for example, one to nine percent. The circuit board 312 in an example comprises a rigid or flexible circuit board. An exemplary circuit board 312 comprises one or more ASICs (application specific integrated circuits) 314 and one or more system connectors 316.

The direct conversion layer as the upstream layer 302 in an example is operable in any one or more of an energy integrating mode and/or a photon counting mode. Exemplary configurations comprise photon counting (PC) only, PC or energy integrating (EI), and PC and EI. EI in an example serves to overcome saturation due to pileup. In an exemplary implementation, the direct conversion layer operates only in the photon counting mode with multiple energy thresholds to register counts in multiple regions of the x-ray spectra. In another exemplary implementation, the direct conversion layer is operable dynamically from a photon counting mode in one view to an integrating mode in another view within the same scan. Such a configurable mode implementation may serve to avoid saturation due to pileup that is characteristic of the photon counting mode. An exemplary ASIC 314 or combinations of ASICs 314 may implement a mode of simultaneous processing of the direct conversion signal charge from the direct conversion layer, for example, to register both integration mode and multiple energy threshold photon counting mode. An exemplary implementation employs a photon counting mode to provide multiple energy data with enhanced, desired, selected, and/or good dose efficiency, and the exemplary implementation employs the integration mode to avoid and/or decrease pileup saturation, with the photon counting mode and the integration mode cooperating and/or serving to provide enhanced, increased, improved, and/or greater dynamic range capability.

An exemplary indirect conversion layer as the downstream layer 304 comprises indirect conversion layer, material, and/or sensor 318, one or more optical couplers 320, one or more photodiode arrangements 322, one or more ASICs 324, and one or more system connectors 326. In an exemplary implementation, the DAS 32 comprises the ASIC 324. The indirect conversion sensor 318 in an example comprises a segmented scintillator pack and/or a segmented pack that comprises a scintillator arrangement and/or a collimator arrangement. Exemplary materials for the indirect conversion sensor 318 comprise Ce (cerium)-activated rare earth garnets, Eu (europium)-activated rare earth oxides, cesium iodide, cadmium tungstate, and/or gallolidium oxysulfide (GOS).

An exemplary thickness of the indirect conversion sensor 318 in a general direction of the beam of x-rays 16 is in an approximate range of 1.0 mm to 4.0 mm, for example, 3.0 mm. In another example, the indirect conversion sensor 318 as the downstream layer 304 comprises a material thickness that serves and/or is sufficient to stop ninety percent or more of the x-rays transmitted through the direct conversion sensor 310 as the upstream layer 302 and incident to the indirect conversion sensor 318 as the downstream layer 304. The photodiode arrangement 322 in an example comprises a plurality of pixels and/or contacts 504, for example, ten to twenty x-direction by twenty to eighty z-direction pixels and/or contacts 504. An exemplary pixel and/or contact 504 comprises a backlit diode and/or major dimensions on the downstream face 504 of approximately 1.0 mm width by 1.0 mm length. An exemplary support 308 comprises a mechanical, thermal, and/or removable support.

The upstream layer 302 in an example obtains ED information in a low and/or high approximate energy range of the beam of x-rays 16. The downstream layer 304 in an example obtains ED information in the low and/or high approximate energy range of the beam of x-rays 16 transmitted through the upstream layer 302 and absorbed in the downstream layer 304.

For comparison, the technique of using dual kVp is typically used with a single layer detector to obtain ED information in two separate acquisitions. This dual kVp technique obtains the low energy range from operating the x-ray source 14 at 80 to 100 kVp and the high energy range from operating the x-ray source 14 at 100 to 140 kVp. An exemplary photon counting energy discriminating detector as the ED detector 20 may have an upstream layer 302 operating in photon counting mode. Operation in the photon counting mode identifies a threshold between the low and high energy ranges at approximately 60-80 keV for the x-ray source 14 operated between 100 to 140 kVp. For example, all energies below 60 keV may be recorded in the low range and all energies above 80 keV may be recorded in the high range. An exemplary dual layer detector as the ED detector 20 may obtain low energy information from an upstream layer 302 and high energy information from a downstream layer 304. For an exemplary layered detector as the ED detector 20 that comprises a direct conversion sensor 310 as an upstream layer 302 and operating in photon counting mode, both low and high energy ranges are available from each layer that comprises the direct conversion sensor 310.

In an exemplary layered system as the system 10, ED information of different energy ranges may be available from different layers as the upstream layer 302 and the downstream layer 304. Exemplary photon counting layers with multiple thresholds as the upstream layer 302 may comprise multiple energy ranges. A data processing algorithm implemented in computer 36 will appropriately combine the energy range data from upstream layer 302 and downstream layer 304 to produce basis material decomposition density information.

Figure 7:
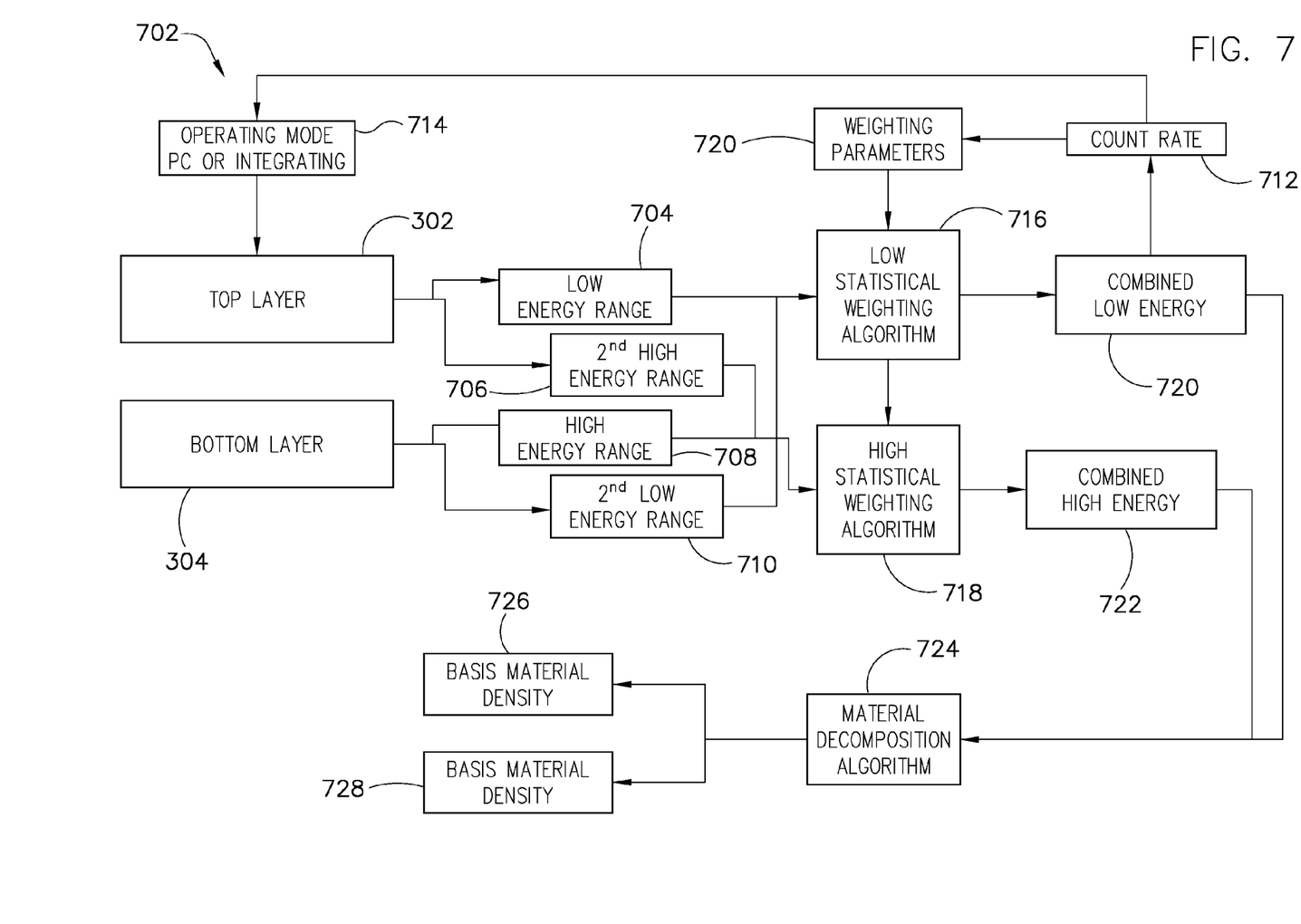
FIG. 7 is a representation of an exemplary logic flow for employment of information from direct and indirect conversion layers of the ED detector of FIG. 3 to achieve energy discrimination.

FIG. 7 is a representation of an exemplary algorithm, procedure, program, process, mechanism, engine, model, coordinator, module, application, code, and/or logic 702 for combining low and high energy range data 704, 706, 708, 710. The logic 702 in an example serves to combine ED information from the upstream layer 302 and the downstream layer 304 to extract a basis material decomposition density for two materials, for example, for each pixel and view. Hardware of an ASIC 314 for the DAS 32 and/or signal processing circuits and/or software of the system computer 36 in an example comprise and/or serve to effect and/or perform an exemplary implementation of the logic 702.

The logic 702 in an example combines the low energy range data 704 from the upstream layer 302 and low energy range data 710 from the downstream layer 304, for example, with a low-range statistical weighting 716. The logic 702 in an example combines the high energy range data 706 from the upstream layer 302 and high energy range data 708 from the downstream layer 304, for example, with a high-range statistical weighting 718. The statistical weighting 716 and/or 718 in an example comprises and/or employ a table lookup and/or calculation, for example, based on weighting parameters 720 that in an example may be affected by the count rate 712 such that only statistically valid data is combined in the statistical weighting 716 and/or 718. Exemplary outputs from the low-range statistical weighting 716 and the high-range statistical weighting 718 comprise combined low-energy data 720 and combined high-energy data 722.

Count rate 712 in an example serves to determine an operating mode 714 for a direct conversion sensor 310 as the upstream layer 302. The count rate 712 in an example comprises an actual or predicted count rate of photons in the beam of x-rays 16. For example, count rate 712 includes the actual count rate of photons determined from the combined low-energy data 720. In another example, count rate 712 includes a predicted count rate of photons for a subsequent view statistically determined from a number of photon count rates from previous views. The statistical determination may be based on a linear or on a non-linear statistical analysis. Exemplary operating modes 714 for the direct conversion sensor 310 as the upstream layer 302 comprise photon counting or integrating operating modes. In an example, the direct conversion sensor 310 may be dynamically switched to operate in a photon counting mode if the actual or predicted count rate is less than approximately 100 million counts per second per millimeter squared. Also, the direct conversion sensor 310 may be dynamically switched to operate in an integration mode if the actual or predicted count rate is greater than approximately 100 million counts per second per millimeter squared. The switching threshold will typically be in the range of 5-100 million counts per second per millimeter squared. The DAS 32 in an example couples the ED information from the upstream layer 302 and the downstream layer 304 of the ED detector 20 to the computer 36. The computer 36 in an example employs the ED information to perform material decomposition of the object 22.

An exemplary material decomposition algorithm 724 employs the combined low-energy data 720 and combined high-energy data 722 to create material basis densities 726 and 728 for two respective materials, as will be appreciated by those skilled in the art. An alternative multi-bin strategy for the material decomposition algorithm 724 takes as direct inputs the signals 704, 706, 708, 710 from the two layers 302 and 304 and incorporates information about the actual or expected count rates 712 to combine these data to generate basis material densities 726 and 728.

In an exemplary implementation, the logic 702 combined with an exemplary layered construction and/or formation for the ED detector 20 serves to provide increased, enhanced, and/or improved material decomposition capability through photon counting in the direct conversion sensor 310 while further maintaining a desired and/or selected level of operation to high flux rates with energy integration. The pileup saturation phenomena of a photon counting layer as the direct conversion sensor 310 in the upstream layer 302 in an example is mitigated by use of integrating information for an alternate operating mode of the upstream layer 302 and/or the indirect conversion sensor 318 of the downstream layer 304 that does not saturate. An exemplary combination of data from the photon counting layer of the direct conversion sensor 310 and the one or more integrating layers in the direct conversion sensor 310 and the indirect conversion sensor 318 in an example serves to enhance, increase, and/or improve dose efficiency in material decomposition, for example, relative to a single direct conversion layer or two integrating layers alone. An exemplary photon counting layer with multiple energy thresholds in the direct conversion sensor 310 serves to provide additional, increased, enhanced, and/or improved energy range information, for example, relative to the information provided by two integrating layers alone.

Figure 8:
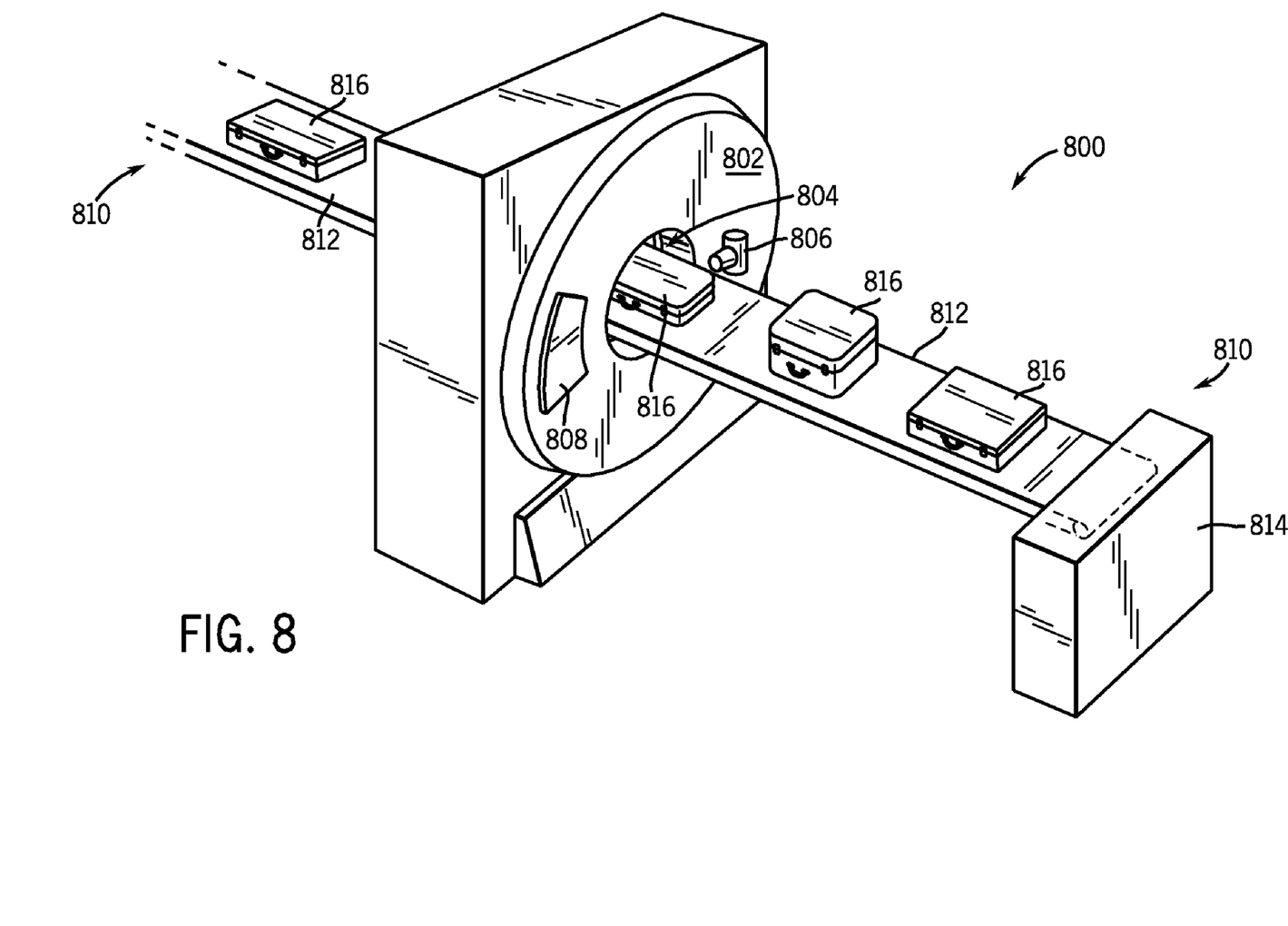
FIG. 8 is a pictorial view of a CT system for use with a non-invasive package inspection system.

Referring now to FIG. 8, package/baggage inspection system 800 includes a rotatable gantry 802 having an opening 804 therein through which packages or pieces of baggage may pass. The rotatable gantry 802 houses an x-ray and/or high frequency electromagnetic energy source 806 as well as a detector assembly 808 having scintillator arrays comprised of scintillator cells. A conveyor system 810 is also provided and includes a conveyor belt 812 supported by structure 814 to automatically and continuously pass packages or baggage pieces 816 through opening 804 to be scanned. Objects 816 are fed through opening 804 by conveyor belt 812, imaging data is then acquired, and the conveyor belt 812 removes the packages 816 from opening 804 in a controlled and continuous manner. As a result, postal inspectors, baggage handlers, and other security personnel may non-invasively inspect the contents of packages 816 for explosives, knives, guns, contraband, etc.

An implementation of the system 10 and/or 800 in an example comprises a plurality of components such as one or more of electronic components, hardware components, and/or computer software components. A number of such components can be combined or divided in an implementation of the system 10 and/or 800. An exemplary component of an implementation of the system 10 and/or 800 employs and/or comprises a set and/or series of computer instructions written in or implemented with any of a number of programming languages, as will be appreciated by those skilled in the art. An exemplary technical effect is one or more exemplary and/or desirable functions, approaches, and/or procedures. An implementation of the system 10 and/or 100 in an example comprises any (e.g., horizontal, oblique, or vertical) orientation, with the description and figures herein illustrating an exemplary orientation of an implementation of the system 10 and/or 800, for explanatory purposes.

An implementation of the system 10 and/or the system 800 encompasses an article. The article comprises one or more computer-readable signal-bearing media. The article comprises means in the one or more media for one or more exemplary and/or desirable functions, approaches, and/or procedures.

An implementation of the system 10 and/or the system 800 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 800 comprises the recordable data storage medium of the image reconstructor 34, and/or the mass storage device 38 of the computer 36. A computer-readable signal-bearing medium for an implementation of the system 10 and/or the system 800 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 800, for instance, one or more of a telephone network, a local area network ("LAN"), a wide area network ("WAN"), the Internet, and/or a wireless network.

The steps or operations described herein are examples. There may be variations to these steps or operations without departing from the spirit of the invention. For example, the steps may be performed in a differing order, or steps may be added, deleted, or modified.

Therefore, according to an embodiment of the present invention, a diagnostic imaging system includes a high frequency electromagnetic energy source that emits a beam of high frequency electromagnetic energy toward an object to be imaged. An energy discriminating (ED) detector receives high frequency electromagnetic energy emitted by the high frequency electromagnetic energy source. The ED detector includes a direct conversion layer dynamically operable in a photon counting mode in one view and in an integrating mode in another view and an indirect conversion layer. A data acquisition system (DAS) is operably connected to the ED detector and a computer operably connected to the DAS.

According to another embodiment of the present invention, a diagnostic imaging detector includes a stacked arrangement of a direct conversion layer and an indirect conversion layer. The direct conversion layer is located between a radiographic energy source and the indirect conversion layer and is operable dynamically from a photon counting mode in one view to an integrating mode in another view.

According to yet another embodiment of the present invention, a method of CT imaging includes emitting an x-ray beam through a subject to be scanned and toward a CT detector having a direct conversion layer and an indirect conversion layer and acquiring energy data from the direct conversion layer and from the indirect conversion layer. The method further includes determining a photon count rate based on the acquired energy data and dynamically configuring the direct conversion layer to operate in one of a photon counting mode and an integrating mode based on the photon count rate.

The present invention has been described in terms of the preferred embodiment, and it is recognized that equivalents, alternatives, and modifications, aside from those expressly stated, are possible and within the scope of the appending claims.

What is claimed is:

1. A diagnostic imaging system, comprising:
    a high frequency electromagnetic energy source that emits a beam of high frequency electromagnetic energy toward an object to be imaged;
    an energy discriminating (ED) detector that receives high frequency electromagnetic energy emitted by the high frequency electromagnetic energy source, wherein the ED detector comprises:
        a direct conversion layer; and
        an indirect conversion layer;
    a data acquisition system (DAS) operably connected to the ED detector;
    a computer operably connected to the DAS; and
    a processor programmed to dynamically operate the direct conversion layer in a photon counting mode in one view and in an integrating mode in another view based on one of an actual count rate and a predicted count rate of photons in the beam of high frequency electromagnetic energy.

2. The diagnostic imaging system of claim 1 wherein the direct conversion layer obtains first ED information from at least one first approximate energy level and/or range of the beam of high frequency electromagnetic energy emitted by the high frequency electromagnetic energy source, and wherein the indirect conversion layer obtains second ED information from at least one second approximate energy level and/or range of the beam of high frequency electromagnetic energy emitted by the high frequency electromagnetic energy source.

3. The diagnostic imaging system of claim 2 wherein the DAS couples the first and second ED information from the ED detector to the computer, wherein the computer operably connected to the DAS is programmed to employ the first and second ED information to perform material decomposition of the object.

4. The diagnostic imaging system of claim 3 wherein the computer is further programmed to combine the first and second ED information with weighting parameters that are a function of predicted or actual count rate.

5. The diagnostic imaging system of claim 1 wherein the direct conversion layer comprises a photon counting detector having multiple energy thresholds, the photon counting detector configured to provide at least one approximate energy level and/or range of the beam of high frequency electromagnetic energy emitted by the high frequency electromagnetic energy source to the DAS.

6. The diagnostic imaging system of claim 1 wherein the indirect conversion layer comprises one or more scintillators and one or more photodiodes.

7. The diagnostic imaging system of claim 1 wherein the direct conversion layer is operably located between the high frequency electromagnetic energy source and the indirect conversion layer.

8. The diagnostic imaging system of claim 1 wherein the direct conversion layer comprises an upstream layer relative to the indirect conversion layer for receipt of the beam of high frequency electromagnetic energy emitted by the high frequency electromagnetic energy source;
    wherein the indirect conversion layer comprises a downstream layer relative to the direct conversion layer for receipt of the beam of high frequency electromagnetic energy emitted by the high frequency electromagnetic energy source; and
    wherein the upstream layer stops less than approximately seventy percent of incident photons of the beam of high frequency electromagnetic energy emitted by the high frequency electromagnetic energy source.

9. The diagnostic imaging system of claim 1 wherein the direct conversion layer comprises an upstream layer relative to the indirect conversion layer for receipt of the beam of high frequency electromagnetic energy emitted by the high frequency electromagnetic energy source;
    wherein the indirect conversion layer comprises a downstream layer relative to the direct conversion layer for receipt of the beam of high frequency electromagnetic energy emitted by the high frequency electromagnetic energy source; and
    wherein the upstream layer stops greater than approximately seventy percent of incident photons of the beam of high frequency electromagnetic energy emitted by the high frequency electromagnetic energy source.

10. The diagnostic imaging system of claim 1 wherein the direct conversion layer comprises a monolithic crystal.

11. The diagnostic imaging system of claim 10 wherein the monolithic crystal of the direct conversion layer comprises a monolithic semiconductor crystal that comprises a thickness in a general direction of the beam of high frequency electromagnetic energy emitted by the high frequency electromagnetic energy source of 0.1 mm to 1.0 mm.

12. A diagnostic imaging detector, comprising:
    a stacked arrangement of a direct conversion layer and an indirect conversion layer;
    wherein the direct conversion layer is located between a radiographic energy source and the indirect conversion layer; and
    a signal processing circuit configured to dynamically switch operation of the direct conversion layer between a photon counting mode and an integrating mode based on an actual or a predicted count rate of photons in an x-ray beam.

13. The diagnostic imaging system of claim 12 wherein the signal processing circuit is configured to dynamically switch the direct conversion layer to be operable in the photon counting mode for the actual or predicted count rate less than approximately 100 million counts per second per millimeter squared and to dynamically switch the direct conversion layer to be operable in the integration mode for actual or predicted flux rates greater than approximately 100 million counts per second per millimeter squared.

14. The diagnostic imaging system of claim 12 wherein the direct conversion layer stops less than approximately seventy percent of incident photons of the beam of high frequency electromagnetic energy emitted by the high frequency electromagnetic energy source.

15. The diagnostic imaging system of claim 12 wherein the direct conversion layer stops greater than approximately seventy percent of incident photons of the beam of high frequency electromagnetic energy emitted by the high frequency electromagnetic energy source.

16. A method of CT imaging comprising the steps of:
    emitting an x-ray beam through a subject to be scanned and toward a CT detector having a direct conversion layer and an indirect conversion layer;
    acquiring energy data from the direct conversion layer and from the indirect conversion layer;
    determining a photon count rate based on the acquired energy data; and
    dynamically configuring the direct conversion layer to operate in one of a photon counting mode and an integrating mode based on the photon count rate.

17. The method of CT imaging of claim 16 wherein the step of determining the photon count rate comprises the step of determining an actual photon count rate from the acquired energy data.

18. The method of CT imaging of claim 16 wherein the step of determining the photon count rate comprises the step of determining a predicted photon count rate for a subsequent view from the acquired energy data.

19. The method of CT imaging of claim 18 wherein the step of determining the predicted photon count rate comprises performing one of a linear statistical analysis and a non-linear statistical analysis on photon count rates from previous views.

20. The method of CT imaging of claim 16 wherein the step of dynamically configuring the direct conversion layer comprises dynamically configuring the direct conversion layer to operate in a photon counting mode if the photon count rate is less than approximately 100 million counts per second per millimeter squared.

21. The method of CT imaging of claim 16 wherein the step of dynamically configuring the direct conversion layer comprises dynamically configuring the direct conversion layer to operate in an integration mode if the photon count rate is greater than approximately 100 million counts per second per millimeter squared.

* * * * *